(12) United States Patent  (10) Patent No.: US 8,460,180 B1
Zarate et al.  (45) Date of Patent: Jun. 11, 2013

(54) ENDOSCOPIC LENS CLEANER

(76) Inventors: Hector Zarate, San Antonio, TX (US);
Robert Lucio, San Antonio, TX (US);
Justin Kilpatrick, Pittsburgh, PA (US);
Nirav Desai, Fort Wayne, IN (US)

( * ) Notice: Subject to any disclaimer, the term of this patent is extended or adjusted under 35 U.S.C. 154(b) by 30 days.

(21) Appl. No.: 13/088,418

(22) Filed: Apr. 18, 2011
(Under 37 CFR 1.47)

Related U.S. Application Data

(60) Provisional application No. 61/342,657, filed on Apr. 16, 2010.

(51) Int. Cl.
*A61B 1/00* (2006.01)
(52) U.S. Cl.
USPC ............................ 600/127; 600/129; 600/176
(58) Field of Classification Search
USPC .................................. 600/157, 127, 129, 176
See application file for complete search history.

(56) References Cited

U.S. PATENT DOCUMENTS

| 7,316,683 | B2 * | 1/2008 | Kasahara et al. | 606/45 |
| 2006/0199998 | A1 * | 9/2006 | Akui et al. | 600/127 |
| 2009/0024121 | A1 * | 1/2009 | Kasahara et al. | 606/39 |
| 2009/0240111 | A1 * | 9/2009 | Kessler et al. | 600/155 |

* cited by examiner

*Primary Examiner* — John P Leubecker
*Assistant Examiner* — Arnaldo Torres Diaz
(74) *Attorney, Agent, or Firm* — John F Horvath (57) ABSTRACT

An endoscopic lens cleaning apparatus includes an end cap, a lens, first and second magnets, one or more guide rails to couple housings for the first and second magnets, and a wiper assembly that is attached to and capable of gliding along the guide rail. The wiper assembly houses a wiper magnet that interacts with the first and second magnets. At least one of the wiper magnet or first and second magnets is an electromagnet, coupled to a power supply via a switch. A controller alternates the polarity of current supplied to the electromagnet to cause the wiper assembly to glide along the rail. A wiper attached to the wiper assembly likewise glides along the lens, thereby cleaning it. The controller is programmable, and can operate in continuous, intermittent, or as needed cleaning modes.

15 Claims, 7 Drawing Sheets

ENDOSCOPIC LENS CLEANER

RELATED APPLICATION

This application claims priority to U.S. Provisional Patent Application Ser. No. 61/342,657, filed on Apr. 16, 2010, entitled "Endoscopic Lens Cleaner," which is herein incorporated by reference in its entirety.

BACKGROUND

Endoscopes are used for a variety of purposes. In general, endoscopes are used to view confined spaces, which are often both dark and dirty. A typical use is in the medical field, where endoscopes are used by doctors to view body cavities in both diagnostic and surgical procedures. Endoscopes are used in many other fields as well. For example, plumbers use endoscopes to inspect pipes, mechanics to inspect engines, and architects to visualize and walk-through scale models of proposed buildings.

Figure 1:
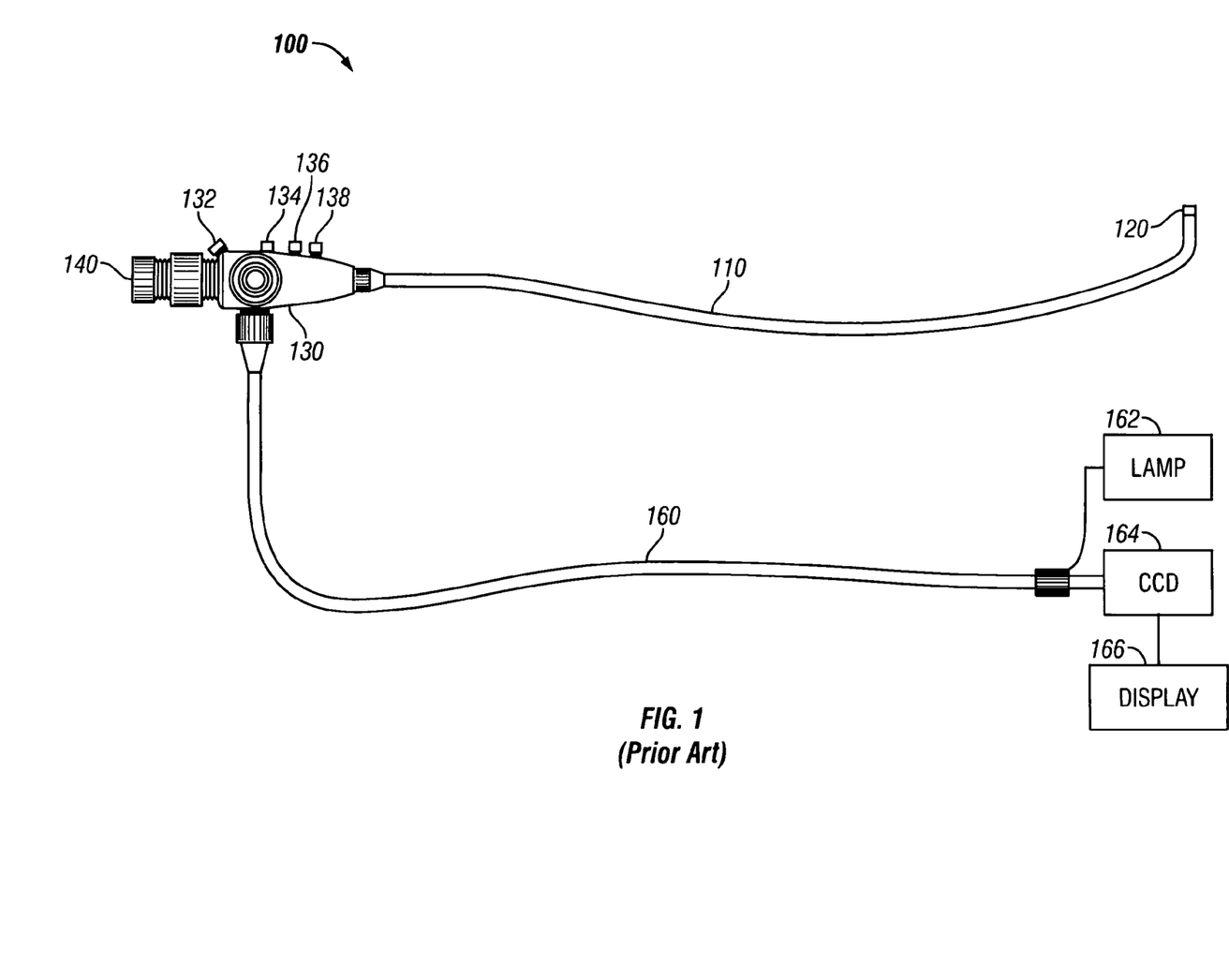
FIG. 1 is a schematic illustration of a prior art endoscope 100.

The components of a typical endoscope 100 are shown in FIG. 1. Endoscope 100 consists of a rigid or flexible tube 110, having an imaging lens 120 at one end, a grip 130 connected to an eyepiece 140 at the other end, and an optical channel (not shown) that optically couples the imaging lens 120 to the eyepiece 140. The grip 130 can include one or more openings 132, through which various instruments can be inserted and carried to the end of tube 110. For example, various medical instruments such as forceps and scalpels can be passed to the end of tube 110 through openings 132. One or more controls 134-138 can be mounted on grip 130 to control the operation of endoscope 100 or instruments attached to endoscope 100. Endoscope 100 can also include an additional optical channel provided through a second rigid or flexible tube 160 to connect the imaging lens 120 to a charge coupled device (CCD) 164. The CCD 164 can be connected to a display or monitor 166 to provide a digital display of the space observed through imaging lens 120. The optical channel through either the tubes 110 or 160 can be a relay lens system (for rigid tubes) or a fiber optic cable (for flexible tubes), neither of which are shown. Typically, endoscope 100 also includes a light delivery system to illuminate the space observed. For example, endoscope 100 can include an LED (not shown) attached to the end of tube 110, or an additional fiber optic cable through tubes 110 and 160 that carries light from a lamp 162 to the end of tube 110.

As mentioned above, a typical use of endoscope 100 is to view a confined space or an object within a confined space that is both dark and dirty. Thus, when in use, it is often necessary to periodically remove endoscope 100 from the space being observed to clean imaging lens 120. This need to periodically clean imaging lens 120 adds an additional element of complexity to whatever procedure is being performed with endoscope 100. For example, when endoscope 100 is used to perform a surgical procedure, any tissue that is being held by forceps attached to endoscope 100 must be released before endoscope 100 can be removed and imaging lens 120 cleaned. Moreover, when endoscope 100 is reinserted into the cavity from which it was removed, additional material may be deposited on imaging lens 120, thus decreasing visibility of the space being observed and requiring an additional removal of endoscope 100 so that imaging lens 120 can be cleaned again.

SUMMARY

An endoscopic lens cleaning apparatus is disclosed. In one embodiment, the lens cleaning apparatus includes an end cap, a lens, first and second magnets, one or more guide rails to couple housings for the first and second magnets, and a wiper assembly that is attached to and capable of gliding along the guide rail. The wiper assembly houses a wiper magnet that interacts with the first and second magnets. At least one of the wiper magnet or first and second magnets is an electromagnet, and coupled to a power supply via a switch. A controller alternates the polarity of current supplied to the electromagnet to cause the wiper assembly to glide along the rail between the housing for the first and second magnets. A wiper attached to the wiper assembly thereby glides along the surface of the lens and cleans it. The controller is programmable, and can operate in continuous, intermittent, or as needed cleaning modes.

BRIEF DESCRIPTION OF THE DRAWINGS

Elements having the same numerals in the several figures refer to the same elements.

DETAILED DESCRIPTION

Currently, when endoscopes such as the prior art endoscope 100 shown in FIG. 1 are used in dirty environments, they must be periodically removed to clean any particulate debris or liquids that build up on imaging lens 120. This increases the time, complexity, and expense of any operation (whether surgical or not) for which endoscope 100 is deployed. To reduce the time, complexity and expense of such operations, an improved endoscope 200 having an end cap 220 that houses a lens cleaning apparatus is provided.

Figure 2:
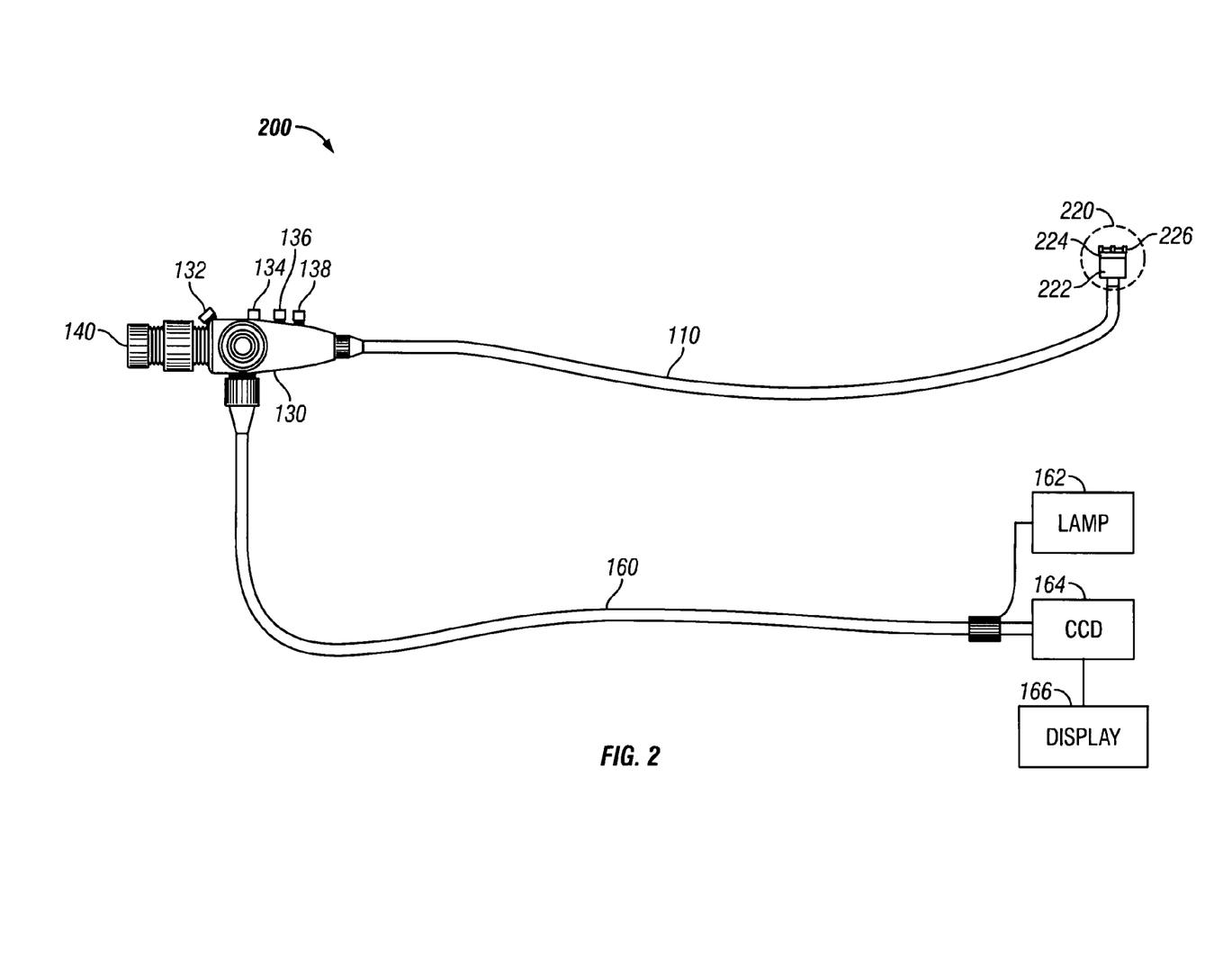
FIG. 2 is a schematic illustration of an improved endoscope 200 having an end cap 220 that houses a lens cleaning apparatus 226.

As shown in FIG. 2, endoscope 200 generally includes all of the component parts of endoscope 100 shown in FIG. 1, and additionally includes an end cap 220 that houses a lens cleaning apparatus 226. End cap 220 includes a base 222, a lens 224 and a lens cleaning apparatus 226. To allow the entire end cap 220 to be easily removed from endoscope 200, the rigid or flexible tube 110 (FIG. 1) can be replaced with a modified flexible tube 210 that is threaded on one end. The base 222 can also be threaded to allow end cap 220 to be screwed onto tube 210, thereby allowing end cap 220 to be easily removed from endoscope 200 and replaced. For example, when endoscope 200 is used in medical procedures, end cap 220 can be easily removed and replaced to help prevent the spread of disease. More detailed schematic illustrations of end cap 220 are shown in FIGS. 3 and 4A through 4C.

Figure 3:
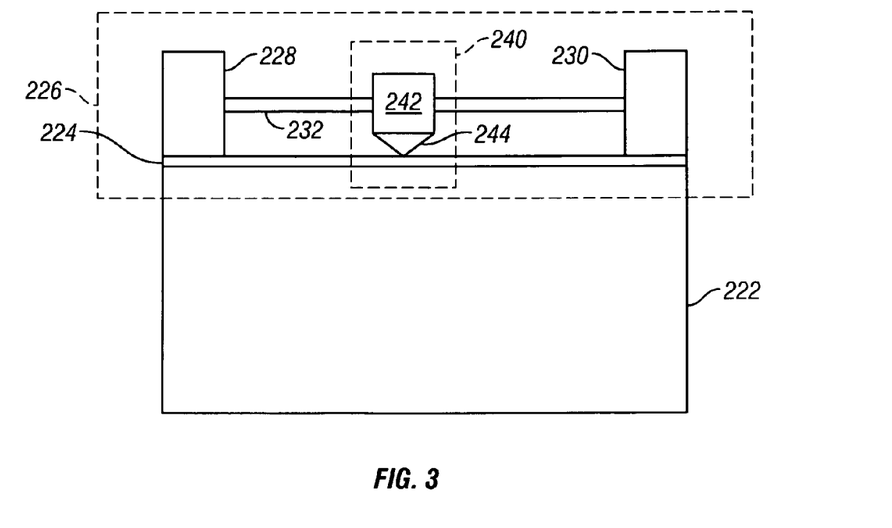
FIG. 3 is a schematic illustration of a generic embodiment of end cap 220.

As shown in FIG. 3, end cap 220 includes base 222, lens 224, and lens cleaning apparatus 226. Lens cleaning apparatus 226 includes a first push-pull magnet 228 (preferably enclosed in a housing), a second push-pull magnet 230 (preferably enclosed in a housing), a pair of guide rails 232 and 234 (not shown) coupled to the housings for the first and second push-pull magnets 228 and 230, and a wiper assembly 240 that is mounted on and capable of gliding along guide rails 232 and 234. Wiper assembly 240 includes a wiper magnet 242 and a wiper blade 244 that rests atop lens 224. When wiper assembly 240 glides along guide rails 232 and 234, wiper blade 244 glides along lens 224, thereby cleaning lens 224 by removing any particulate debris or fluid that obstructs the view through lens 224. Each of the first and second push-pull magnets 228 and 230, as well as the wiper assembly magnet 242, can be embodied as either a permanent magnet (e.g., made from a ferromagnetic material) or as an electromagnet. However, at least one of the wiper magnet 242, push-pull magnet 228, or push-pull magnet 230 must be implemented as an electromagnet to provide the movement necessary to clean lens 224.

Figure 4A:
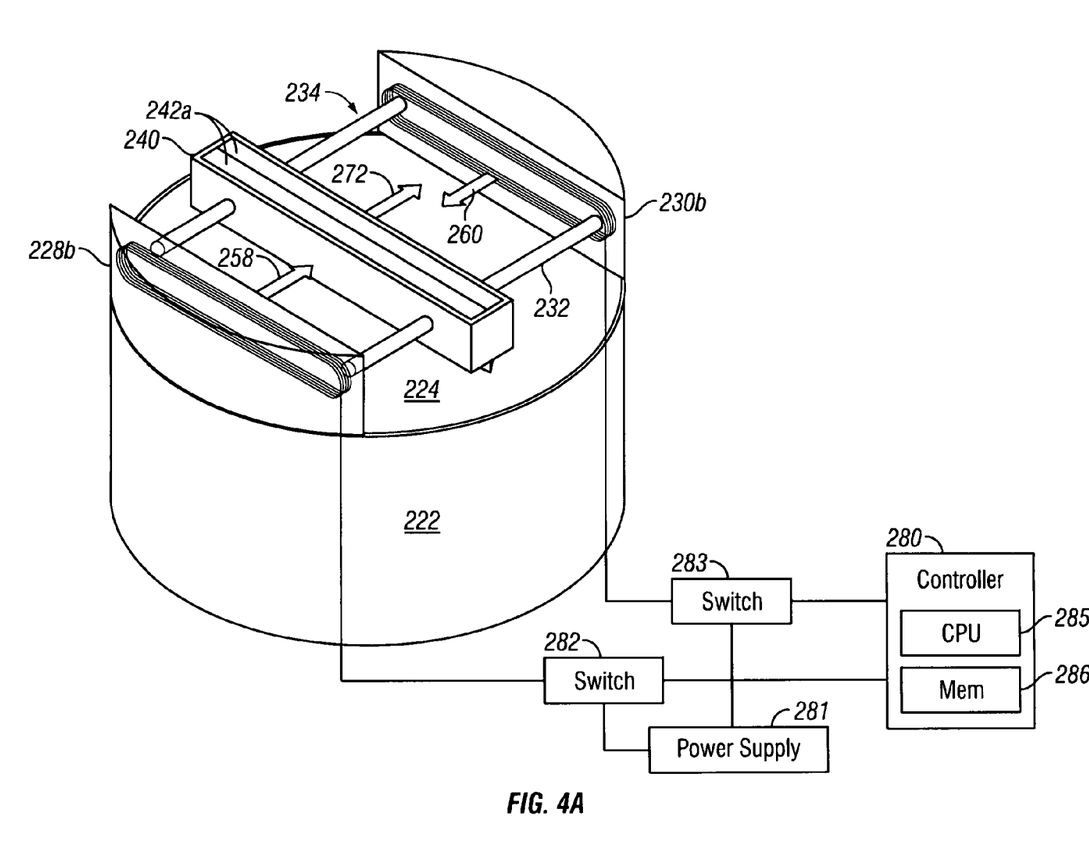
FIG. 4A is a schematic illustration of a first embodiment of end cap 220.

In a first embodiment, shown in FIG. 4A, wiper magnet 242 is embodied as a permanent wiper magnet 242a. Any suitable material, such as iron or a rare-earth metal, can be used to make permanent wiper magnet 242a. The permanent wiper magnet 242a is seated in its housing so that the north pole of its dipole moment 272 faces one of the push-pull magnets (e.g., push-pull magnet 230b), while the south pole of its dipole moment 272 faces the other one of the push-pull magnets (e.g., push-pull magnet 228). Each of push-pull magnets 228 and 230 are embodied as electromagnets 228b and 230b. Push-pull electromagnets 228b and 230b are wound so that when they are supplied a current of a first polarity (e.g., a positive polarity current), they produce dipole magnetic fields having respective dipole moments 258 and 260 that are aligned (or anti-aligned) with the dipole moment 272 of the magnetic field produced by permanent wiper magnet 242a, and when they are supplied a current of opposite polarity (e.g., a negative polarity current), they produce dipole magnetic fields having respective dipole moments 258 and 260 that are anti-aligned (or aligned) with the dipole moment 272 of the magnetic field produced by permanent wiper magnet 242a. Each of the electromagnets 228b and 230b can be connected to a power supply 281, such as a dual polarity power supply, through respective switches 282 and 283 to receive either a positive or negative polarity current. Switches 282 and 283, which can be for example MOSFET transistors, are further connected to a controller 280. Controller 280 can be any suitable controller, and generally includes a processor or CPU 285 coupled to a memory 286. Controller 280 or CPU 285 can be programmed to control both the polarity and the duration of the current supplied to each of push-pull electromagnets 228b and 230b through their respective switches 282 and 283. Memory 286 can be either RAM or ROM, and contains suitable instructions or code that, when executed by CPU 285, allows controller 280 to control lens cleaning apparatus 226 as described below.

To move wiper assembly 240 away from push-pull electromagnet 228b along guide rails 232 and 234, controller 280 can instruct switch 282 to supply electromagnet 228b with a current of the proper polarity to generate a dipole magnetic field having a dipole moment 258 that is anti-aligned with the dipole moment 272 of the magnetic field produced by permanent wiper magnet 242a. The resulting dipole-dipole repulsion between push-pull electromagnet 228b and permanent wiper magnet 242a will cause wiper assembly 240 to glide along guide rails 232 and 234 in the direction of push-pull electromagnet 230b. At the same time, controller 280 can also instruct switch 283 to supply electromagnet 230b with a current of the proper polarity (which can be the same as or opposite to the polarity supplied to electromagnet 228b depending on how the two electromagnets are wound) in order to generate a magnetic field having a dipole moment 260 that is aligned with the dipole moment 272 of the magnetic field produced by permanent wiper magnet 242a. The resulting dipole-dipole attraction between push-pull electromagnet 230b and permanent wiper magnet 242a will also cause the wiper assembly 240 to glide along guide rails 232 and 234 in the direction of push-pull electromagnet 230b. As wiper assembly 240 glides along guide rails 232 and 234, wiper blade 244 will glide along lens 224, thereby cleaning the lens.

When wiper assembly 240 reaches push-pull magnet 230b, it must be moved back in the direction of push-pull magnet 228b to continue cleaning lens 224. The motion back toward push-pull magnet 228b can be done immediately if lens 224 needs continual cleaning, can be delayed for a programmable period of time if lens 224 needs only intermittent cleaning, or can be delayed indefinitely while awaiting instructions from an operator of endoscope 200 to clean lens 224 as needed. In any event, to move wiper assembly 240 back toward push-pull electromagnet 228b, controller 280 can instruct switch 282 to supply electromagnet 228b with a current of the proper polarity (which will be opposite the polarity required to move wiper assembly 240 away from push-pull electromagnet 228b), to generate a magnetic field having a dipole moment 258 that is aligned with the dipole moment 272 of the magnetic field produced by permanent wiper magnet 242a. The resulting dipole-dipole attraction between push-pull electromagnet 228b and permanent wiper magnet 242a will cause wiper assembly 240 to glide along guide rails 232 and 234 in the direction of push-pull electromagnet 228b. At the same time, controller 280 can also instruct switch 283 to supply electromagnet 230b with a current of the proper polarity (which will again be opposite the polarity required to move wiper assembly 240 toward push-pull electromagnet 230b) in order to generate a magnetic field having a dipole moment 260 that is anti-aligned with the dipole moment 272 of the magnetic field produced by permanent wiper magnet 242a. The resulting dipole-dipole repulsion between push-pull electromagnet 230b and permanent wiper magnet 242a will also cause wiper assembly 240 to glide along guide rails 232 and 234 in the direction of push-pull electromagnet 228b. As before, while wiper assembly 240 glides along guide rails 232 and 234, wiper blade 244 will glide along lens 224, thereby cleaning the lens.

Figure 4B:
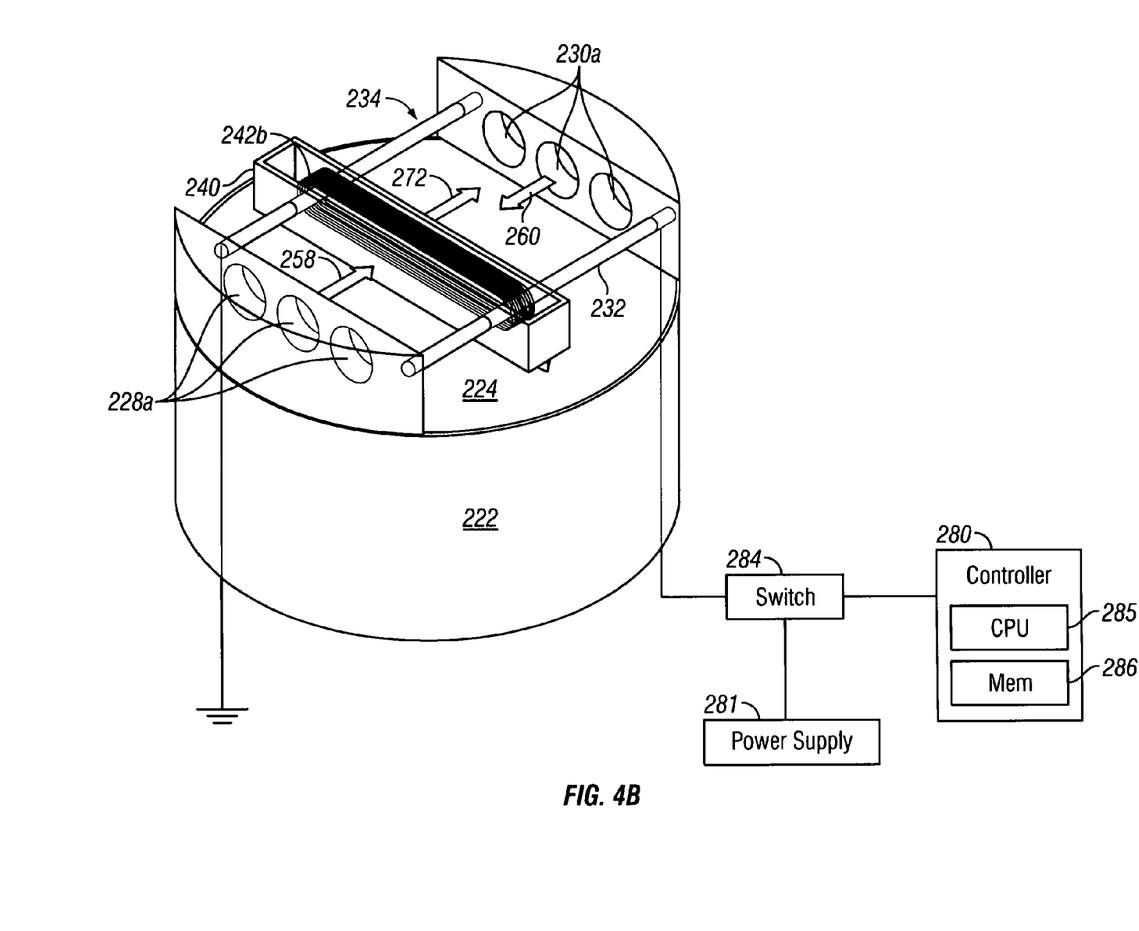
FIG. 4B is a schematic illustration of a second embodiment of end cap 220.

In a second embodiment, shown in FIG. 4B, wiper magnet 242 can be embodied as a wiper electromagnet 242b, while push-pull magnets 228 and 230 are embodied as permanent push-pull magnets 228a and 230a. Again, any suitable material, such as iron or a rare-earth metal, can be used to implement permanent push-pull magnets 228a and 230a. The permanent push-pull magnets 228a and 230a are seated in their housings so that one their respective dipole moments 258 and 260 faces the wiper assembly 240. The wiper electromagnet 242b is wound so that when it is supplied a current of a first polarity (e.g., a positive polarity current), it generates a dipole magnetic field having a dipole moment 272 that is aligned with the dipole moment of the magnetic field produced by one of the permanent push-pull magnets (e.g., push-pull magnet 228a), and when it is supplied a current of opposite polarity (e.g., a negative polarity current), it generates a magnetic field having a dipole field 272 that is aligned with the dipole moment of the magnetic field produced by the other permanent push-pull magnet (e.g., push-pull magnet 230a).

The wiper electromagnet 242b can receive current of either polarity from a power supply 281 (which can be a dual polarity power supply) through guide rails 232 and 234. In this embodiment, guide rails 232 and 234 must be made from a suitable conductive material, such as aluminum. Electrical contact between the coil of electromagnetic wiper magnet 242b and guide rails 232 and 234 can be provided through brushes. Guide rails 232 and 234 can be connected to power supply 281 through a switch 284 that can be further connected to controller 280. Switch 284 can be, for example, a MOSFET transistor. Controller 280 can be programmed to control both the polarity and the duration of the current supplied to electromagnetic wiper magnet 242b through switch 284.

To move wiper assembly 240 away from permanent push-pull magnet 228a along guide rails 232 and 234 in the second embodiment, controller 280 can instruct switch 284 to supply wiper electromagnet 242b with a current of the proper polarity (e.g., a positive polarity current), to generate a magnetic field having a dipole moment 272 that is anti-aligned with the dipole moment 258 of the magnetic field produced by permanent push-pull magnet 228a and aligned with the dipole moment 260 of the magnetic field produced by permanent push-pull magnet 230a. The resulting dipole-dipole repulsion between permanent push-pull magnet 228a and wiper electromagnet 242b and dipole-dipole attraction between permanent push-pull electromagnet 230a and wiper electromagnet 242b will cause wiper assembly 240 to glide along guide rails 232 and 234 in the direction of permanent push-pull magnet 230a. As wiper assembly 240 glides along guide rails 232 and 234, wiper blade 244 will glide along lens 224, thereby cleaning the lens.

Once the wiper assembly 240 reaches permanent push-pull magnet 230a, wiper assembly 240 must be moved back in the direction of push-pull magnet 228a in order to continue cleaning lens 224. As before, the motion back toward permanent push-pull magnet 228a can be done immediately if lens 224 needs continual cleaning, can be delayed for a programmable period of time if lens 224 needs only intermittent cleaning, or can be delayed indefinitely while awaiting instructions from an operator of endoscope 200 to further clean the lens as needed. In any event, to move wiper assembly 240 back toward permanent push-pull magnet 228a, controller 280 can instruct switch 284 to supply wiper electromagnet 242b with a current of the proper polarity (which will be opposite the polarity required to move wiper assembly 240 away from permanent push-pull 228a), to generate a magnetic field having a dipole moment 272 that is aligned with the dipole moment 258 of the magnetic field produced by permanent push-pull magnet 228a and anti-aligned with the dipole moment 260 of the magnetic field produced by permanent push-pull magnet 230a. The resulting dipole-dipole attraction between permanent push-pull magnet 228a and wiper electromagnet 242b and dipole-dipole repulsion between permanent push-pull magnet 230a and wiper electromagnet 242b will cause the wiper assembly 240 to glide along guide rails 232 and 234 in the direction of permanent push-pull electromagnet 228a. As before, while wiper assembly 240 glides along guide rails 232 and 234, wiper blade 244 will glide along lens 224, thereby cleaning the lens.

Figure 4C:
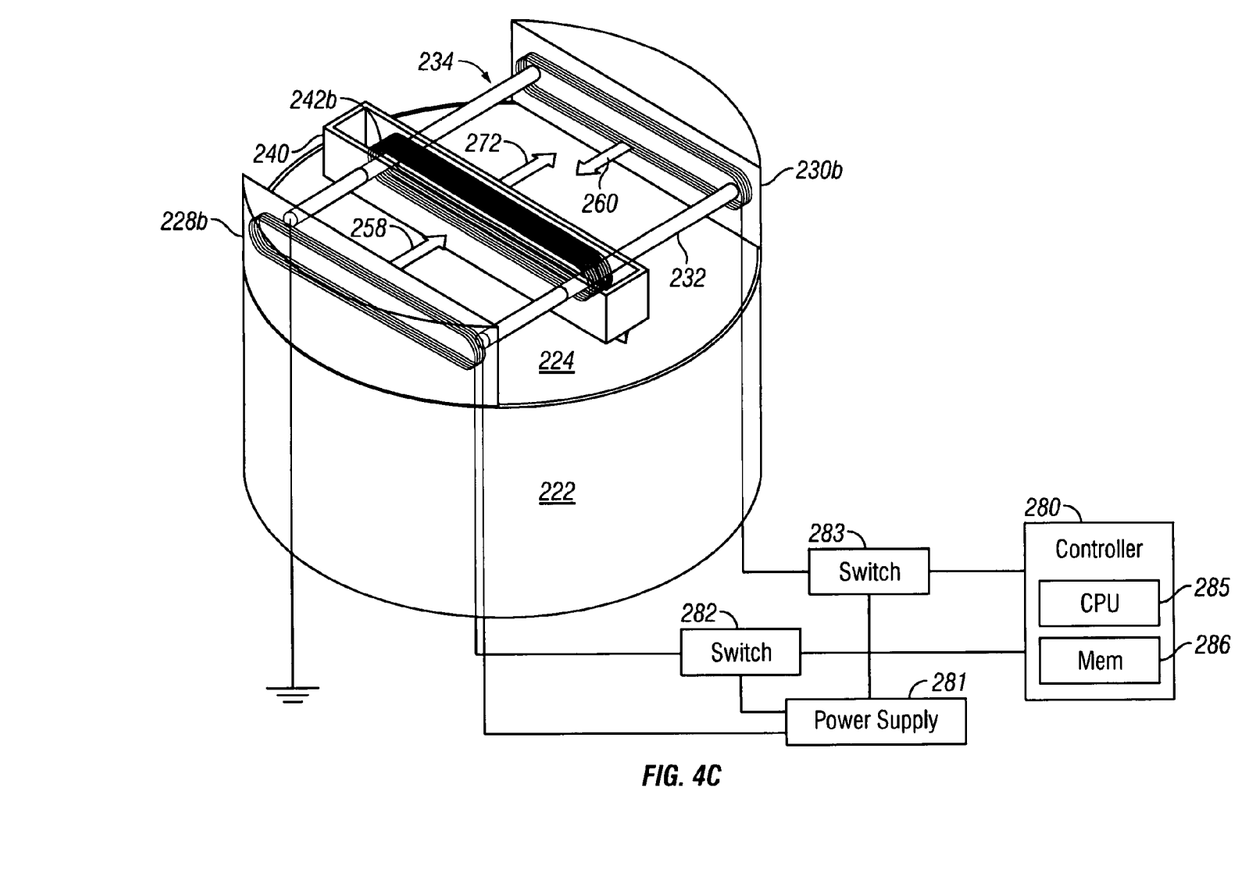
FIG. 4C is a schematic illustration of a third embodiment of end cap 220.

In a third embodiment, shown in FIG. 4C, wiper magnet 242 and push-pull magnets 228 and 230 can be respectively embodied as electromagnets 242b, 228b and 230b. Wiper electromagnet magnet 242b is wound so that when it is supplied a current of a first polarity (e.g., a positive polarity current), its dipole moment 272 is either aligned or anti-aligned with the dipole moments 258 and 260 produced by respective push-pull magnets 228b and 230b when they are supplied a current of either polarity in the plane of lens 224. Push-pull electromagnets 228b and 230b are wound so that when they are supplied a current of a first polarity (e.g., a positive polarity current), their resulting dipole moments 258 and 260 are respectively aligned and anti-aligned (or vice-versa) with the dipole moment 272 of wiper electromagnet 242b, and when they are supplied a current of opposite polarity (e.g., a negative polarity current), their resulting dipole moments 258 and 260 are respectively anti-aligned and aligned (or vice-versa) with the dipole moment 272 of wiper electromagnet magnet 242b.

Each of the electromagnets 228b, 230b and 242b are connected to a power supply 281, such as a dual polarity power supply. Wiper electromagnet 242b is connected to power supply 281 to receive a current of a first polarity (e.g., a positive polarity current), while push-pull electromagnets 228b and 230b are connected to power supply 281 through respective switches 282 and 283 to receive either a positive or negative polarity current. Switches 282 and 283, which can be embodied as a MOSFET transistor, are further connected to a controller 280, which can be programmed to control both the polarity and the duration of the current supplied to each of push-pull electromagnets 228b and 230b through their respective switches 282 and 283.

To move wiper assembly 240 away from push-pull electromagnet 228b along guide rails 232 and 234, controller 280 can instruct switch 282 to supply electromagnet 228b with a current of the proper polarity (e.g., a positive polarity current), to generate a magnetic field having a dipole moment 258 that is anti-aligned with the dipole moment 272 of the magnetic field produced by wiper electromagnet 242b. The resulting dipole-dipole repulsion between push-pull electromagnet 228b and wiper electromagnet 242b will cause wiper assembly 240 to glide along guide rails 232 and 234 in the direction of push-pull electromagnet 230b. At the same time, controller 280 can also instruct switch 283 to supply push-pull electromagnet 230b with a current of the proper polarity (which can be the same as or opposite to the polarity supplied to electromagnet 228b depending on how the two electromagnets are wound) in order to generate a magnetic field having a dipole moment 260 that is aligned with the dipole moment 272 of the magnetic field produced by wiper electromagnet 242b. The resulting dipole-dipole attraction between push-pull electromagnet 230b and wiper electromagnet 242b will also cause the wiper assembly 240 to glide along guide rails 232 and 234 in the direction of push-pull electromagnet 230b. As wiper assembly 240 glides along guide rails 232 and 234, wiper blade 244 will glide along lens 224, thereby cleaning the lens.

Once the wiper assembly 240 reaches push-pull electromagnet 230b, wiper assembly 240 must be moved back in the direction of push-pull electromagnet 230b in order to continue cleaning lens 224. The motion back toward push-pull electromagnet 230b can be done immediately if lens 224 needs continual cleaning, can be delayed for a programmable period of time if lens 224 needs only intermittent cleaning, or can be delayed indefinitely while awaiting instructions from an operator of endoscope 200 to further clean lens 224 as needed. In any event, to move wiper assembly 240 back toward push-pull electromagnet 228b, controller 280 can instruct switch 282 to supply electromagnet 228b with a current of the proper polarity (which will be opposite the polarity required to move wiper assembly 240 away from push-pull electromagnet 228b), to generate a magnetic field having a dipole moment 258 that is aligned with the dipole moment 272 of the magnetic field produced by wiper electromagnet 242b. The resulting dipole-dipole attraction between push-pull electromagnet 228b and wiper electromagnet 242b will cause the wiper assembly 240 to glide along guide rails 232 and 234 in the direction of push-pull electromagnet 228b. At the same time, controller 280 can also instruct switch 283 to supply electromagnet 230b with a current of the proper polarity (which will again be opposite the polarity required to move wiper assembly 240 toward push-pull electromagnet 230b) in order to generate a magnetic field having a dipole moment 260 that is anti-aligned with the dipole moment 272 of the magnetic field produced by wiper electromagnet 242b. The resulting dipole-dipole repulsion between push-pull electromagnet 230b and wiper electromagnet 242b will also cause the wiper assembly 240 to glide along guide rails 232 and 234 in the direction of push-pull electromagnet 228b. As before, while wiper assembly 240 glides along guide rails 232 and 234, wiper blade 244 will glide along lens 224, thereby cleaning the lens.

As described above, lens cleaning apparatus 226 can operate in several different cleaning modes, including a continuous cleaning mode in which wiper assembly 240 continually moves back and forth between push-pull magnets 228 and 230, an intermittent cleaning mode in which wiper assembly 240 intermittently pauses at either or both of push-pull magnets 228 and 230, and an as needed cleaning mode in which wiper assembly 240 pauses indefinitely at either or both of push-pull magnets 228 and 230. The three modes of operation can be programmed into controller 280. As shown in FIG. 2, a mode control 134 situated on grip 130 of endoscope 200 can be manipulated by a user of endoscope 200 to select the mode of operation.

Additional controls placed on grip 130 of endoscope 200 can be manipulated to provide further control of lens cleaning apparatus 226 in each of the operating modes. For example, when operating in continuous cleaning mode, a frequency control 136 can be manipulated by a user of endoscope 200 to select a frequency with which wiper assembly 240 oscillates between push-pull magnets 282 and 283. Frequency control 136 can be a continuous control (e.g., a varactor or variable resistor), to allow selection of an operating frequency from among a continuum of operating frequencies. Alternatively, frequency control 136 can be a discrete control (e.g., a switch) to allow selection of an operating frequency from among a discrete set of operating frequencies.

When lens cleaning apparatus 226 is operated in intermittent cleaning mode, frequency control 136 can be used to select the frequency of a pulse train having a duty cycle that is defined by the product of the selected frequency and the duration or width of each pulse in the pulse train. The width of pulses in the pulse train can be selected via a duty cycle control 138 on grip 130 of endoscope 200. As with frequency control 136, duty cycle control 138 can be either a continuous control to allow the selection of a pulse width from among a continuum of pulse widths, or a discrete control to allow the selection of a pulse width from among a discrete set of pulse widths.

When lens cleaning apparatus 226 is operated in as needed cleaning mode, an additional control (not shown) on grip 130 of endoscope 200 can be used to limit the amount of time wiper assembly 240 is permitted to move. This can be done, for example, by simply interrupting the power supplied to any of the magnets 228, 230 or 242 (when embodied as electromagnets), or by selecting the number of pulses provided in a current pulse train supplied to the electromagnets. In the latter case, the frequency of the pulse train can be selected via frequency control 136, the pulse width can be selected via duty cycle control 138 (and can be 100% to effect continuous cleaning), and the number of pulses in the pulse train can be selected via the additional control so that the pulse train consists of a discrete number of pulses (e.g., five). Examples of the various current waveforms that can be supplied to the magnets 228, 230 or 242 (when embodied as electromagnets), in order to control the operation of wiper assembly 240 are described below.

Figure 5A:
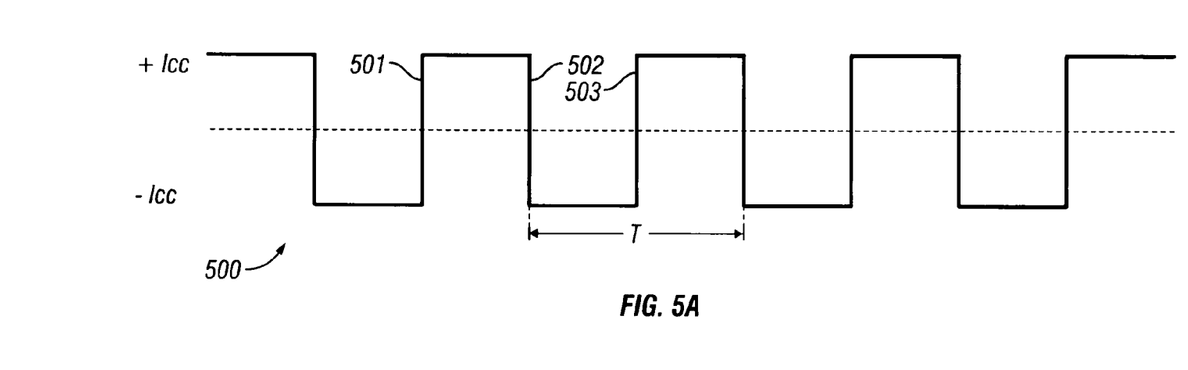
FIG. 5A is a schematic illustration of a waveform that can be used to control the movement of lens cleaning apparatus 226 in a continual cleaning mode.

As shown in FIG. 5A, when mode control 134 is used to select a continuous cleaning mode and frequency control 136 is used to select a cleaning frequency defined by a period T, controller 280 can, upon interpreting the signals sent from mode and frequency controls 134 and 136, send appropriate control signals to one or more switches providing current to one or more of the electromagnets in lens cleaning assembly 226. For example, referring to FIG. 4A, controller 280 can send a control signal to switch 282, enabling switch 282 to provide a current to electromagnet 228b having a waveform 500 that oscillates between a positive polarity (+Icc) and a negative polarity (−Icc) over a period T. Between points 501 and 502 of current waveform 500, the positive polarity current (+Icc) will cause wiper assembly 240 to move from one of the push-pull magnets (e.g., push-pull magnet 228b) toward the other push-pull magnet (e.g., push-pull magnet 230b), while between points 502 and 503 of current waveform 500, the negative polarity current (−Icc) will cause wiper assembly 240 to move back to push-pull magnet 228b. Since current waveform 500 continually oscillates between phases of positive and negative polarity with a period T, wiper assembly 240 will continually oscillate back and forth between the push-pull magnets 228b and 230b with the same period T.

Figure 5B:
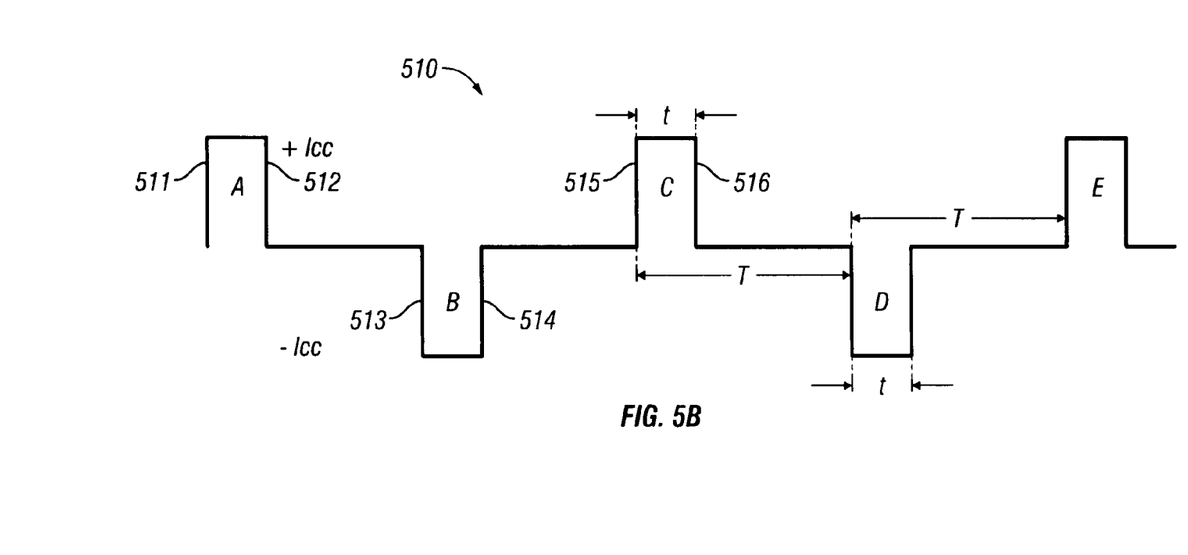
FIG. 5B is a schematic illustration of a waveform that can be used to control the movement of lens cleaning apparatus 226 in an intermittent cleaning mode.

As shown in FIG. 5B, when a mode control 134 is used to select an intermittent cleaning mode, frequency control 136 is used to select a cleaning frequency defined by a period T, and duty cycle control 138 is used to select a pulse width defined by a duration t, controller 280 can interpret the signals sent from the mode, frequency and duty cycle controls 134, 136 and 138, respectively, to send appropriate control signals to switch 282, enabling that switch to provide a current to push-pull electromagnet 228b having a waveform 510. As shown, current waveform 510 consists of a sequence of pulses (e.g., A, B and C) each of which has a duration "t" reflecting the duty cycle selected via duty cycle control 138. In particular, the duty cycle is given by D=t/T, where T is the period T between any two pulses (e.g., A and B), and reflects the frequency selected via frequency control 136. Between points 511 and 512 of current waveform 510, the positive polarity current (+Icc) will cause wiper assembly 240 to move from push-pull magnet 228b toward push-pull magnet 230b. Between points 512 and 513, the lack of current will cause wiper assembly 240 to remain at push-pull magnet 230b for a period of time given by the difference between the period of the current waveform 500 (i.e., T) and the duration of a pulse in the current waveform 500 (i.e., t). Between points 513 and 514 of current waveform 500, the negative polarity current (−Icc) will cause wiper assembly 240 to move back to push-pull magnet 228b. In this fashion, as wiper 244 moves along with wiper assembly 240 across lens 224, it will intermittently clean lens 226.

In FIG. 5B, if the pulse train (A, B, C) is assumed to continue indefinitely, lens cleaning apparatus 226 will continue to operate in the intermittent cleaning mode. If, however, mode control 134 is used to select the as needed cleaning mode, controller 280 can limit the time during which wiper assembly 240 is allowed to glide across lens 224. For example, controller 280 can be programmed to limit the number of pulses in the current waveform 510 shown in FIG. 5B so that only a finite number of pulses are permitted. If only two pulses (e.g., A and B) are permitted, the motion of wiper assembly 240 can thereby be limited to one cycle between push-pull magnets 228b and 230b. Moreover, an additional control (not shown) can be provided on grip 130 to repeat the limited motion of wiper assembly 240 as needed to clean lens 224 by a user of endoscope 200. Alternatively, the additional control can be used to limit the motion of wiper assembly 240 at will, e.g., by interrupting the current supplied to push-pull electromagnet 228b when depressed.

Of course, to simplify the discussion, the examples described above assume control of only one of the electromagnets, i.e., push-pull electromagnet 228b. In general, any of the electromagnets 228b, 230b or 242b described in FIGS. 5A through 5C can be similarly controlled. In some cases, depending on how the electromagnets are wound, the polarities of the signals may need to be reversed to achieve the operations described. Moreover, when two electromagnets are used to move wiper 240, the current signals sent to the two electromagnets would need to be synchronized in order to generate magnetic fields having appropriate dipole moments to respectively push or pull wiper assembly 240 in the desired direction. Such details would be familiar to a person of skill in the art, and easily programmed into controller 280 to achieve the desired result.

Other embodiments for endoscope 200 and lens cleaning apparatus 226 are also possible. For example, while FIGS. 5A through 5C describe embodiments in which wiper assembly 240 is moved along glide rails 232 and 234 by simultaneously pushing wiper magnet 242 away from one push-pull magnet (e.g., push-pull magnet 228) and toward another push-pull magnet (e.g., push-pull magnet 230), in alternative embodiments, wiper assembly 240 can be moved in one direction simply by pushing wiper magnet 242 away from one push-pull magnet (e.g., push-pull magnet 228) and in the opposite direction by pulling wiper magnet 242 toward the same push-pull magnet. In these embodiments, only one push-pull magnet is required (e.g., push-pull magnet 228), and the housing for the other push-pull magnet (e.g., push-pull magnet 230) can be used solely to anchor the guide rails 232 and 234. In another embodiment, two push-pull magnets can be used successively, e.g., by supplying current to only one of the push-pull magnets at a time. For example, current can first be supplied to a near push-pull magnet (e.g., push-pull magnet 228) to push wiper assembly 240 away from the near magnet, and subsequent applied to a far push-pull magnet (e.g., push-pull magnet 230) to pull wiper assembly 240 toward the far push-pull magnet.

Moreover, while two guide rails 232 and 234 are used to guide wiper assembly 240 between the push-pull magnets 228 and 230 in the embodiments shown, a different number of guide rails (e.g., one or three) can be used in alternative embodiments.

The preceding descriptions of specific embodiments of the endoscopic lens cleaning apparatus 226 are presented for purposes of illustration and description. They are not intended to be exhaustive or to limit the invention to the precise forms disclosed. Rather, many modifications and variations are possible in view of the above teachings to those of skill in the art. The embodiments were chosen and described in order to best explain the principles of the invention and its practical applications, and to enable others skilled in the art to best utilize the invention and various embodiments with various modifications as suited to the particular use contemplated.

What is claimed is:

1. An endoscopic lens cleaning apparatus, comprising:
   an end cap for securing the lens cleaning apparatus to an endoscope;
   a lens, coupled to the end cap;
   a first housing and a second housing, seated above and along the periphery of the lens, wherein the second housing is substantially parallel to the first housing;
   a first magnet housed by the first housing and capable of generating a magnetic field having a dipole moment whose principal axis is substantially parallel to the plane of the lens and substantially orthogonal to the first and second housings;
   at least one guide rail coupled to the first and second housings, having a principle axis that is substantially parallel to the plane of the lens and substantially orthogonal to the first and second housings;
   a wiper housing coupled to the at least one guide rail, and configured to glide along the guide rail between the first and second housings;
   a wiper magnet, housed by the wiper housing and capable of generating a magnetic field having a dipole moment whose principal axis is substantially parallel to the plane of the lens and substantially orthogonal to the first and second housings, wherein at least one of the first magnet or the wiper magnet is an electromagnet;
   a wiper, coupled to the wiper housing and extending from the wiper housing to the lens, wherein the wiper is configured to clean the lens when an interaction between the dipole moments of the first magnet and the wiper magnet causes the wiper housing to glide along the at least one guide rail.

2. The endoscopic lens cleaning apparatus of claim 1, wherein the first magnet is an electromagnet, further comprising
   a first switch, coupled to the first magnet and having at least a first state in which the first switch delivers a positive current to the first magnet and a second state in which the first switch delivers a negative current to the first magnet; and
   a controller coupled to the first switch, and configured to send a signal to the first switch to place the first switch in either the first state or the second state.

3. The endoscopic lens cleaning apparatus of claim 2, wherein the controller is programmed to operate the lens cleaning apparatus in at least one of a continuous cleaning mode, an intermittent cleaning mode, or an as needed cleaning mode.

4. The endoscopic lens cleaning apparatus of claim 2, wherein when configured to operate in a continuous cleaning mode, the signal sent by the controller to the first switch alternately places the first switch in the first and second states.

5. The endoscopic lens cleaning apparatus of claim 2, wherein the first switch includes a third state in which the first switch does not deliver current to the first magnet.

6. The endoscopic lens cleaning apparatus of claim 5, wherein when configured to operate in an intermittent cleaning mode, the signal sent by the controller to the first switch places the first switch in the first state for a first period of time and in the third state for a second period of time.

7. The endoscopic lens cleaning apparatus of claim 6, wherein the signal sent by the controller to the first switch is further configured to place the first switch in the second state for the first period of time.

8. The endoscopic lens cleaning apparatus of claim 2, wherein the wiper magnet is either an electromagnet or a permanent magnet.

9. The endoscopic lens cleaning apparatus of claim 1, further comprising a second magnet, housed by the second housing and capable of generating a magnetic field having a dipole moment whose principal axis is substantially parallel to the plane of the lens and substantially orthogonal to the first and second housings.

10. The endoscopic lens cleaning apparatus of claim 9, wherein the first and second magnets are electromagnets, further comprising:
- a first switch, coupled to the first magnet and having at least a first state in which the first switch delivers a positive current to the first magnet and a second state in which the first switch delivers a negative current to the first magnet;
- a second switch, coupled to the second magnet and having at least a first state in which the second switch delivers a positive current to the second magnet and a second state in which the second switch delivers a negative current to the second magnet; and
- a controller coupled to the first and second switches, and configured to send a first signal to the first switch to place the first switch in either the first state or the second state, and to send a second signal to the second switch to place the second switch in either the first state or the second state.

11. The endoscopic lens cleaning apparatus of claim 10, wherein the controller is programmed to operate the lens cleaning apparatus in at least one of a continuous cleaning mode, an intermittent cleaning mode, or an as needed cleaning mode.

12. The endoscopic lens cleaning apparatus of claim 10, wherein when configured to operate in a continuous cleaning mode, the first signal sent by the controller to the first switch alternately places the first switch in the first and second states and the second signal sent by the controller to the second switch alternately places the second switch in the first and second states.

13. The endoscopic lens cleaning apparatus of claim 10, wherein the first switch includes a third state in which the first switch does not deliver current to the first magnet, and the second switch includes a third state in which the second switch does not deliver current to the second magnet.

14. The endoscopic lens cleaning apparatus of claim 13, wherein when configured to operate in an intermittent cleaning mode, the first signal sent by the controller to the first switch places the first switch in the first state for a first period of time and in the third state for a second period of time, and the second signal sent by the controller to the second switch places the second switch in the first state for the first period of time and in the third state for the second period of time.

15. The endoscopic lens cleaning apparatus of claim 14, wherein the first signal sent by the controller places the first switch in the second state for the first period of time, and the second signal sent by the controller places the second switch in the second state for the first period of time.

\* \* \* \* \*